United States Patent [19]

Macecek

[11] 4,395,911
[45] Aug. 2, 1983

[54] METHOD AND APPARATUS FOR PRECISE DETERMINATION OF GIRTH WELD DEFECTS

[75] Inventor: Mirek Macecek, Toronto, Canada

[73] Assignee: American Gas Association, Arlington, Va.

[21] Appl. No.: 244,869

[22] Filed: Mar. 18, 1981

[51] Int. Cl.³ .......................................... G01N 29/04
[52] U.S. Cl. ..................................... 73/622; 73/615
[58] Field of Search ................. 73/622, 610, 611, 615, 73/616, 625, 627, 628, 629, 637, 638, 640, 641

[56] References Cited

U.S. PATENT DOCUMENTS

| 3,213,676 | 10/1965 | Makous | 73/611 |
| 3,552,191 | 1/1971 | Heseding | 73/624 |
| 4,270,389 | 6/1981 | Shiraiwa et al. | 73/622 |

OTHER PUBLICATIONS

A. deSterke, "Automatic Ultrasonic Inspection of Pipeline Welds", *NDT International*, vol. 13, No. 6, pp. 275-284, Dec. 1980.

*Primary Examiner*—Stephen A. Kreitman
*Attorney, Agent, or Firm*—Fitzpatrick, Cella, Harper & Scinto

[57] ABSTRACT

Pulses of accoustic energy are transmitted at normal incidence to the wall of a welded pipe, and also at an oblique angle thereto, wherein such transmissions, from respective transducers, occur immediately adjacent a girth weld. Reflected pulses are then received and processed to analyze the radial extent of the girth weld at each interface between the pipe and the weld material. By these means, undercuts or cracks in the weld are detected and analyzed as to their depth and profile. The energy transmitted normal to the pipe wall determines the distance between the pipe and the pulse transducers, and a signal is then generated to simulate a reflection from the inner wall of the pipe with relation to an obliquely-directed pulse. The transducers are then moved axially of the pipe and towards the weld, in small increments, in order to cause the oblique transmission of pulses finally to intercept the weld, thereby producing reflected pulse data when cracks or undercuts are encountered. The heads are also moved circumferentially of the pipe in order to determine the circumferential extent of any undercut or crack.

10 Claims, 6 Drawing Figures

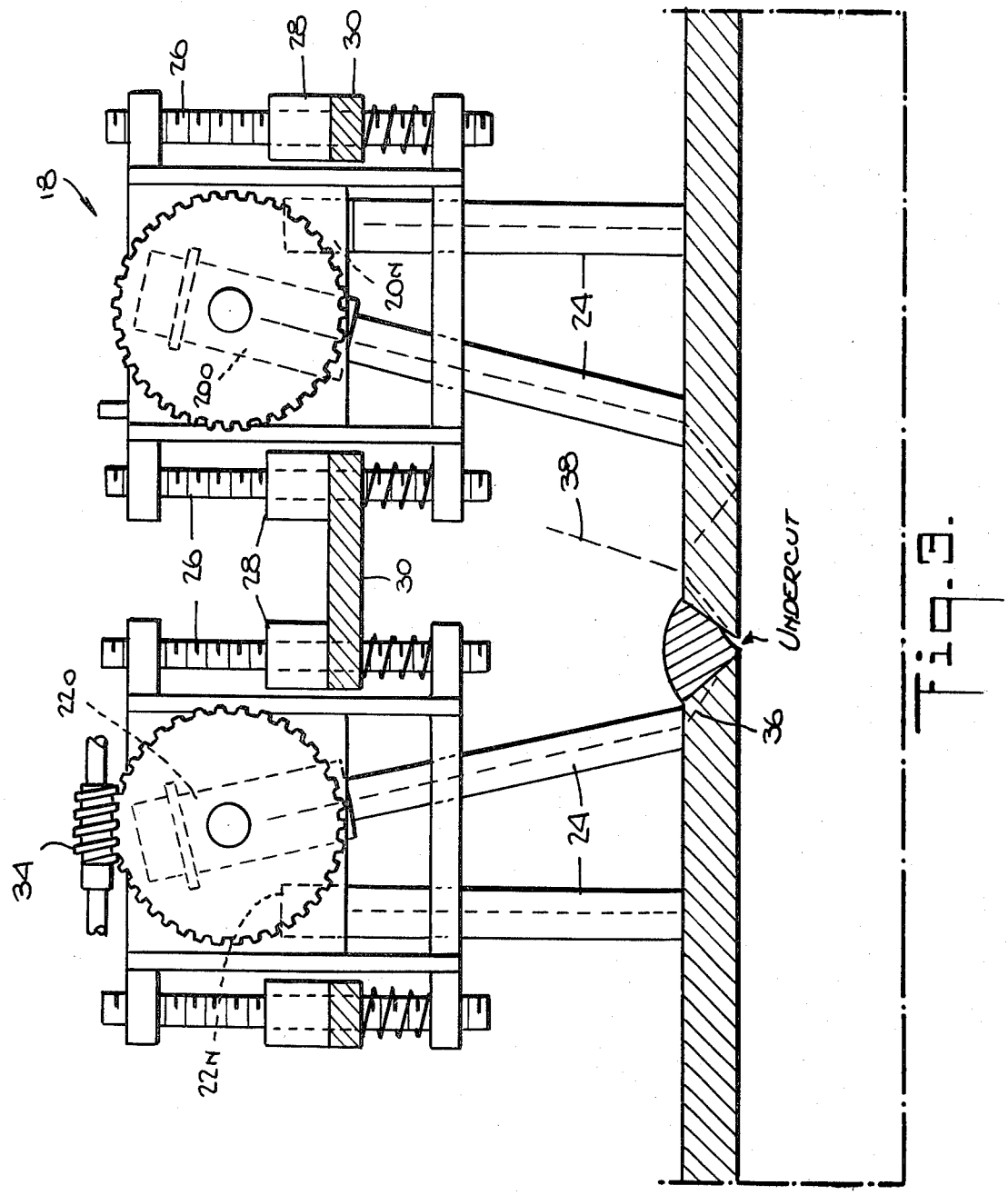

METHOD AND APPARATUS FOR PRECISE DETERMINATION OF GIRTH WELD DEFECTS

BACKGROUND OF THE INVENTION

In the construction of pipe lines wherein elongated pipe sections are welded together by forming girth welds, such welds must be examined for defects utilizing, for example, ultrasonics and X-ray or gamma-ray radiography. However, while the use of such known techniques yield approximate characteristics of the weld defects, as derived from changes in densities of the pipe wall, such techniques do not yield sufficiently accurate data related to the geometry and depth of undercuts or cracks. Specifically, it is believed that such techniques are not sufficiently accurate for providing a precise depth determination of undercuts or toe cracks, as called for by the specifications of the American Petroleum Institute.

An example of such a weld defect, in the form of an undercut, is shown in FIG. 1 of the drawings. Referring specifically to FIG. 1, a cross-section of a butt weld is depicted wherein the ends of two pipe sections are welded together. Prior to effecting the weld a band is affixed to the pipe and a bevel machine is mounted on the band for circumferential movement to provide each pipe and with a beveled surface as indicated. Next, a welding machine may be mounted on the band to effect the weld illustrated in FIG. 1. Due to various causes, defects may occur in the weld, as also illustrated in FIG. 1, wherein an undercut may develop at an inner edge of the weld. While specifications defining permissible limits for such undercuts have been defined by the American Petroleum Institute, and while remedial procedures for such defects have also been specified, it is believed that the state of the art of measuring techniques has not been fully adequate to ensure adherence to such specifications.

For example, in one prior art proposal for inspecting welds, as disclosed in U.S. Pat. No. 3,213,676, a method is described for detecting voids internally of a weld, but the structure and process described in that process is incapable of defining the depth and profile of an undercut as required by the abovementioned specifications of the American Petroleum Institute.

Accordingly, a principal object of the present invention is to provide a method and apparatus for detecting the depth and circumferential extent of flaws in pipe line girth welds. The invention utilizes a novel process and apparatus for transmitting, receiving, and processing acoustic energy pulses in order to provide an accurate profile of weld defects.

SUMMARY OF THE INVENTION

In accordance with a preferred embodiment of the invention an acoustic transducer carriage is provided for reciprocal movement on the surface of a pipe, wherein such movement occurs axially of the pipe and immediately adjacent to a girth weld. The above-described reciprocal movement of the carriage occurs at circumferential steps around the girth of the pipe weld. The carriage holds at least one pair of transducers, one disposed normal to the pipe and the other disposed obliquely thereto, wherein data is collected from reflections of acoustic energy pulses generated by the normal and oblique transducers. The normal transducer provides a pulse which is reflected by the outer surface of the pipe in order to accurately determine the distance between the transducer head and the surface of the pipe. Furthermore, the reflected signal received by the normal transducer is used to generate a signal simulating the time at which a return signal could be expected from the inner wall of the pipe. The simulated inner wall signal is precisely formulated and calibrated by means of measurements obtained by a test piece of the pipe which is to be welded. Such measurements are used to generate a "marker" signal corresponding to the time required for an acoustic pulse to travel from the oblique transducer, to the inner wall of the pipe, and then back to the transducer. By slowly moving the respective transducers, in unison, toward and away from the weld (i.e., axially of the pipe), it is possible to receive and process acoustic pulse energy to determine the angle and depth of one surface of an undercut or crack in the weld face. That is, reflections of pulses generated by the oblique transducer, wherein such reflections are received prior to the generation of corresponding signals simulating the inner wall, may be interpreted as being reflections from an undercut or crack. This concept is described in greater detail in connection with the detailed description of FIG. 3, set forth below.

By moving the transducer carriage circumferentially of the pipe, and adjacent to the girth weld therein, while making the above-described measurements, it is possible to determine the circumferential length of any such crack or undercut.

BRIEF DESCRIPTION OF THE DRAWINGS

A preferred embodiment of the invention will be described in detail in conjunction with the accompanying drawings in which:

FIG. 3 illustrates a schematic cross-section of transducer devices utilized in the defect analyzing device of FIG. 2;

DETAILED DESCRIPTION OF A PREFERRED EMBODIMENT

Figure 1:
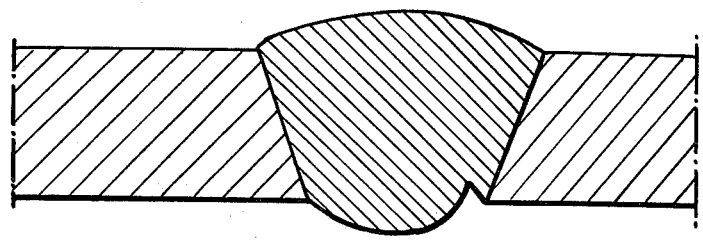
FIG. 1 is a cross-sectional depiction of a pipe weld showing an undercut defect.
Figure 2:
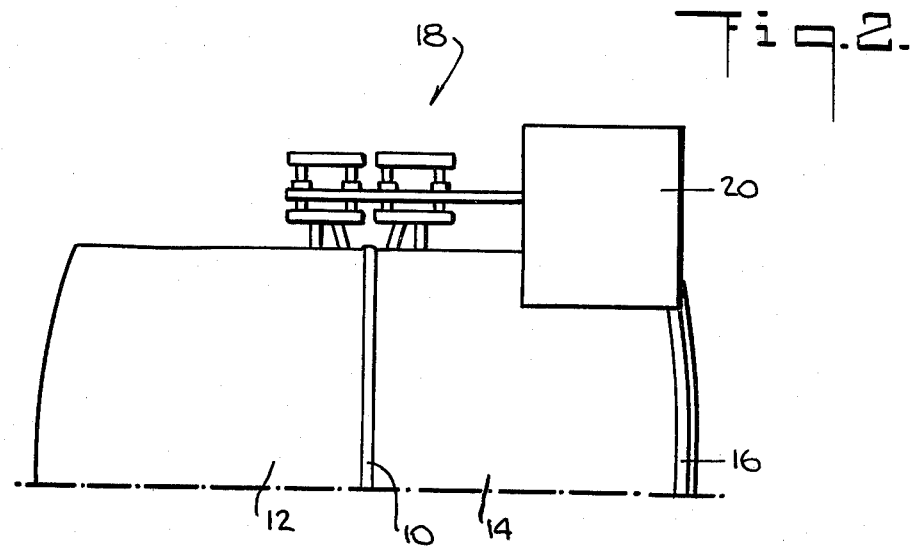
FIG. 2 depicts a perspective view of a weld joint in a pipe line, wherein a defect analyzing device is utilized to scan the weld for undercuts or cracks.

In the construction of a pipe line, such as for use in transporting natural gas, pipe sections which may be about 40' long are welded together about the girth of the pipe. Conventionally, such pipes may range from 8" to 56" in diameter and may have wall thicknesses ranging from $\frac{1}{4}$" to 1". The pipe line, a small portion of which is illustrated in FIG. 2, is constructed by effecting such girth welds 10 at the construction site, for example, immediately adjacent a ditch in which the assembled pipe sections are eventually buried. In this regard, due to the relative inflexibility of the pipe material, the pipe is lowered into the ditch some 300–400 yards upstream from the last completed weld.

The girth weld at each joint between pipe sections 12 and 14 may be formed manually or by a welding machine, as for example, a CRC Crose welding system which is mounted on a welding or bevelling band 16 attached to the pipe 14 at a portion adjacent the ends of the pipe sections which must be welded. Upon completion of the weld 10, a transducer carriage 18 may be mounted on the bevelling band for advancement around the circumference of the pipe, and for this purpose a standard driving system 20, such as used to move a bevelling machine or welder, may be used. Alternatively, such advancement may be effected along a chain-and-sprocket assembly or on a timing belt attached about the circumference of the pipe. In operation, the carriage 18 is reciprocated axially of the pipe line wherein reflected data is gathered and processed to provide the desired profile of any undercut or crack, and the transducer carriage is also advanced circumferentially so that data from such reciprocating movements is gathered around the entire circumference of the weld.

Specifically, a carriage 18 having four transducers mounted thereon, as shown schematically in FIG. 3 of the drawings, may be reciprocated as discussed above. The transducers are arranged in two pairs, one pair on each side of the girth weld, so that the carriage bridges the weld and provides a normal transducer 20N and an oblique transducer 20O on one side and comparable transducers 22N and 22O on the other side. As is apparent from FIG. 3, the transducer in each pair which is outermost from the weld is disposed normal to the surface of the pipe so that acoustic transmissions therefrom are directed at the wall of the pipe in order to precisely determine the distance between such transducer and the pipe surface. Conventionally, all of such transducers comprise ultrasonic focus transducers, available, for example, from Panametrics, and operated at a frequency of about 5–10 MHz. The transducers are controlled to operate at a pulse repetition frequency of about 1–10 KHz having pulse widths of 1–3λ. Furthermore, all of the transducers provide a long focal length in water, and as illustrated in FIG. 3, the transmissions from each of the transducers are projected through water filled tubes 24 in a conventional manner.

As illustrated, each pair of transducers 20 and 22 is mounted to provide for relative movement with respect to the other pair, to compensate for slight misalignments of adjacent pipe sections which are to be welded. Furthermore, each of the obliquely directed transducers may be adjusted with respect to their oblique angle to ensure proper operation as described below.

The relative adjustability of one pair of transducers with respect to the other may be accomplished by standard means, wherein threaded rods 26 are provided on each mounting device for the transducers so that thumb screws 28 may be utilized to vary the height of one set of transducers with respect to the other. Brackets 30 are spring biased against the thumb screws so that transducer pairs at each end of the bridge may be properly and relatively aligned. The oblique transducer, on the other hand, may be held on a swivel plate or roller to change its angle by means of a rack and pinion mechanism.

As also illustrated in FIG. 3, the coupling shoes 24 are disposed between each transducer and the pipe surface in order to hold a quantity of coupling fluid to complete the fluid path between each transducer and the pipe surface. In the depiction of FIG. 3, the bridge 18 has been moved to its extreme rightward position at which point the oblique beam 20O is disposed to commence examining the ultimate depth of a crack or undercut in the right-hand face of the weld. As depicted by the dotted line 36 emanating from the oblique transducer on the left side of the bridge 18, the acoustic energy is transmitted along a line which passes through an extent of continuous and solid pipe and is reflected outwardly and away from the transducers. As the bridge is advanced to the left, the pulses from such oblique transducer 20O will impinge in the lower extent of the undercut shown at the right side of the weld, and a reflected signal will be received and processed by the circuitry of the invention. Furthermore, the oblique transducer on the left side of the bridge 18 will produce a wave which is not reflected along its path of initial transmission. However, as the bridge is advanced to the left the oblique transducer 20O on the right side will contine to direct its beam toward the crack so that the beam is reflected back along its original transmission path by irregularities of the pipe surface at the interface of the undercut on the right side of the weld, as depicted by the dotted line 38. Continued movement by the transducer, in the same direction will permit the reflected signals to scan the entire right-hand face of the undercut, thereby defining its depth and profile.

Figure 4:
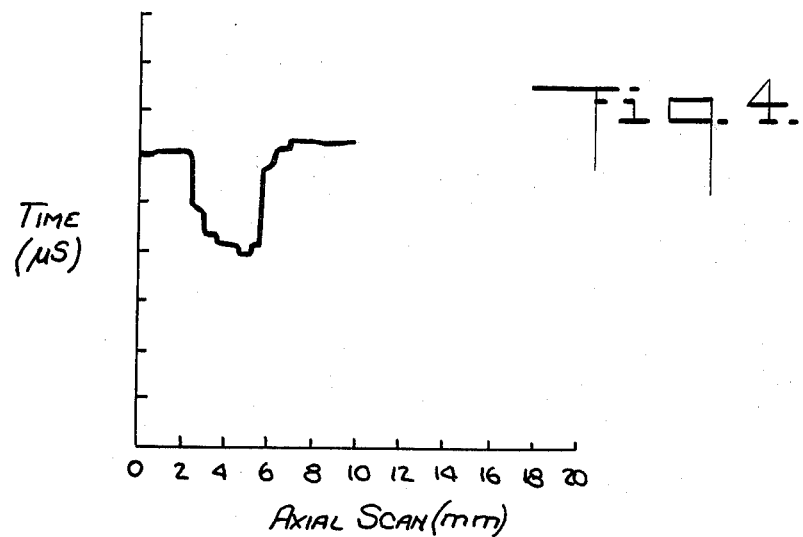
FIG. 4 illustrates a display output which defines the depth and angle of an undercut or crack in the weld material.

Again, in operation, the transducers of normal incidence 20N and 22N will detect the distance between the transducer heads and the pipe surface, whereupon by means of fundamental trigonometric functions, knowing the thickness of the pipe, one can provide a delayed signal, referenced from the reflection from a normal pulse, and corresponding to an echo which would be received from the inner wall. A display may be generated by the signals simulating the inner wall of the pipe, when combined with any echo signals received by the oblique transducers. For example, as shown in FIG. 4, a strip chart or oscillograph presentation may be produced wherein time is measured along the y-axis while distance in millimeters is measured along the x-axis. In this regard, the pulses produced to simulate the inner wall of the pipe are utilized to form the uppermost marker in FIG. 4, and such pulses are recorded at incremental distances measured axially of the pipe as recorded on the x-axis. If an undercut is encountered by the pulses generated by the oblique transducer, a reflected wave will reach the oblique transducer prior to the time of the next succeeding pulse simulating the inner wall. As the oblique transducer moves closer to the weld, echo pulses will be continually produced until the transmission from the oblique transducer passes over the crest of the undercut. Accordingly, it will be appreciated that the resultant wave form from such echo will correspond to that shown in FIG. 4. In a preferred embodiment, for example, a permanent record may be produced for each weld joint in a pipe line by recording wave forms corresponding to FIG. 4 at each one of a plurality of positions about the circumference of the girth weld.

The advancing and returning movement of said transducers may be effected by well-known means comprising for example a stepping motor utilized in conjunction with a worm gear, incorporated in the mechanism 20 for controlling a reciprocating movement of the bridge 20 carrying the transducers. Again, the mechanism for moving the transducer bridge circumferentially, may be identical to known equipment for driving an automatic welding or bevelling device.

Figure 5:
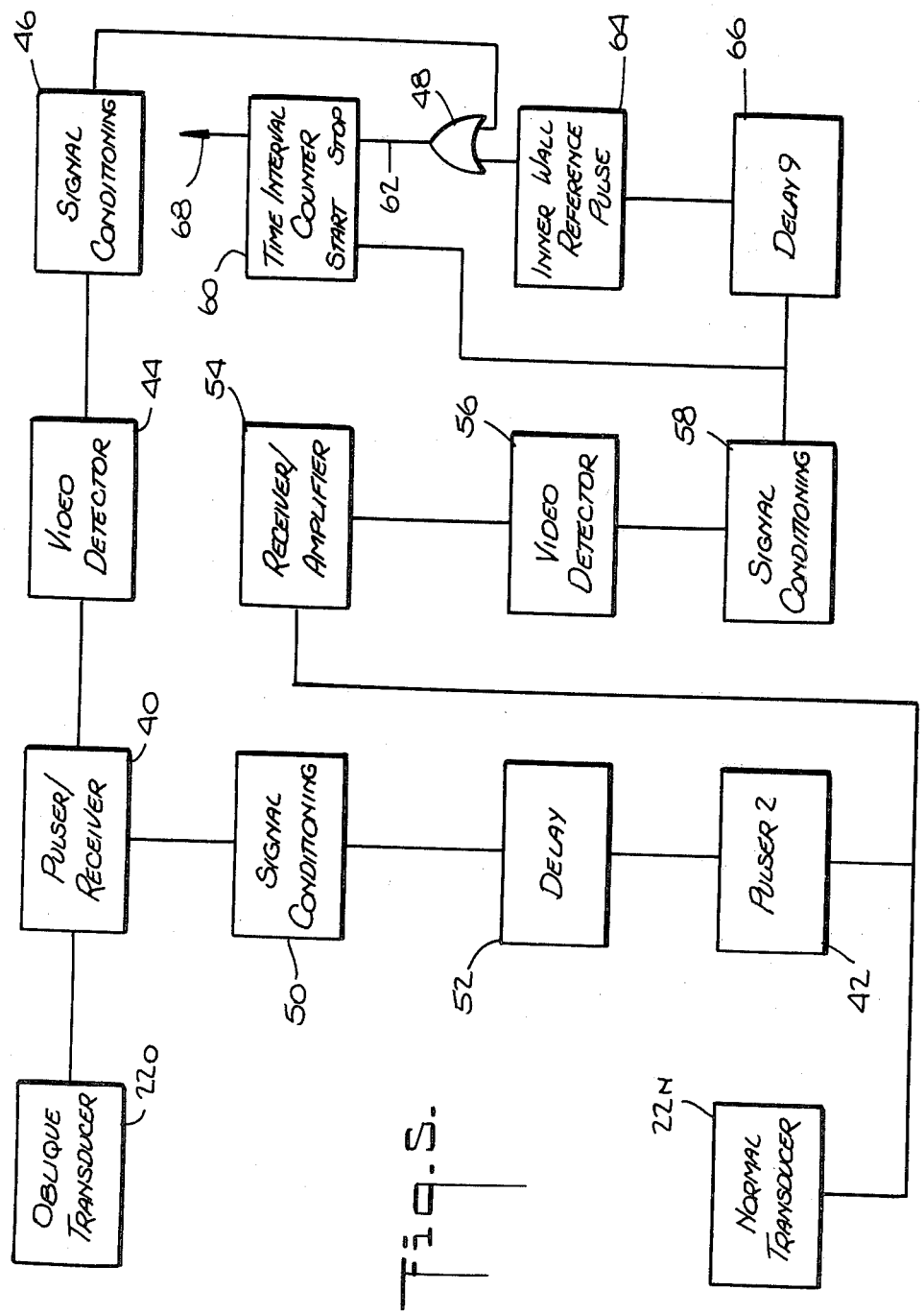
FIG. 5 is a block diagram of the data processing circuitry embodied in the invention.

Circuitry which may be utilized to effect the detection of undercuts or cracks, as described hereinabove, and as depicted in FIG. 5, may comprise oblique and normal transducers 22O and 22N connected to pulsing devices 40 and 42. The pulser 40 connected to the oblique transducer 22O also comprises a gated receiver having an output connected through a video detector 44 and a signal conditioning circuit 46 to one input of an OR circuit 48. The pulser 40 has a second pulse output connected through a signal conditioning circuit 50 and a delay circuit 52 (for avoiding conflicting timing of gate signals) to control the second pulser 42. Each normal transducer is also connected through a receiver/amplifier 54, a video detector 56 and a signal conditioning circuit 58 to the start input of a time interval counter 60. The output 62 of the OR circuit is connected to the stop input of such counter and an "inner wall reference pulse" circuit 64 is connected to a second input of the OR circuit, while the input to such reference pulse circuitry is connected through a delay circuit 66 from the signal conditioning device. In operation, the echo signal received by the normal transducer 22N is utilized as the start signal for the counter 60, while the delay circuitry 66 provides a delay, calculated by the trigonometric functions mentioned above in order to produce the inner wall reference pulse.

Accordingly, it will be appreciated that there will be an output 68 from the time interval counter 60 at each generation of an inner wall reference pulse, with the exception that such an output pulse will be generated earlier if a signal is received from the oblique transducer, and coupled through the OR circuit 48 prior to the receipt of a reset signal due to a simulated inner wall pulse.

Figure 6:
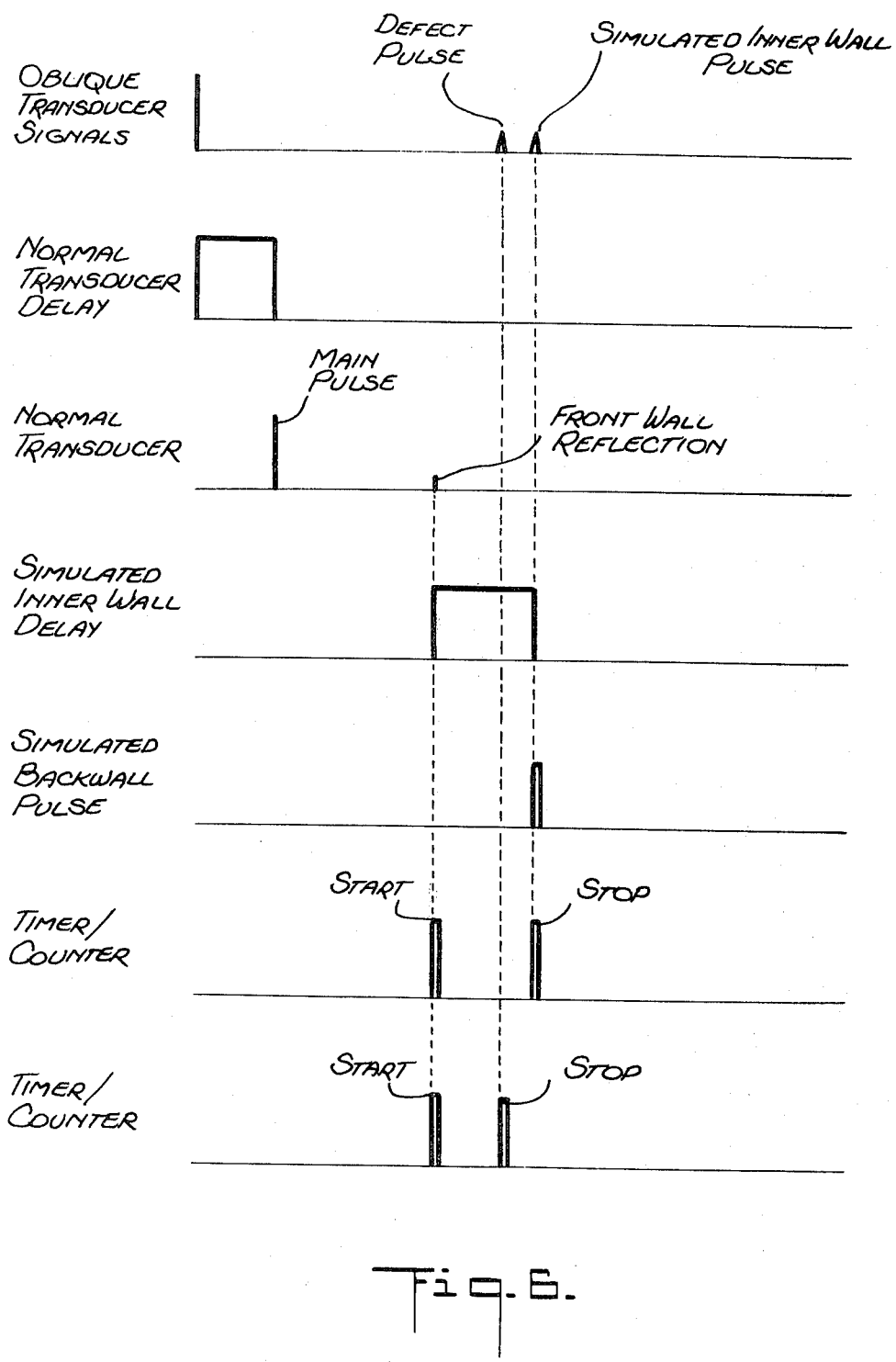
FIG. 6 is a timing chart illustrating the transmitted and received acoustic energy.

Wave forms and pulses corresponding to the above description of operation of the apparatus and circuitry, as illustrated in FIG. 5, are believed to be straightforward, and will be described in conjunction with FIG. 6, wherein the first wave form illustrates a transmitted oblique transducer signal shown in relation to the timing of a reflected defect pulse, and the timing of a simulated inner wall pulse. Immediately below the representation of oblique transducer signals there appears the output of the delay circuit 52 which is applied to the normal transducer. Next depicted is an output pulse from the normal transducer 22N, corresponding in time with the trailing edge of the delay signal. At the same portion of FIG. 5 there is shown a front wall reflection signal, the timing of which, with respect to the main normal pulse, indicates the height of the normal transducer above the outer pipe surface. As described above, that reflected pulse is processed by the receiver amplifier 54, video detector 56, and signal conditioning circuit 58, and then applied to start the counting of the interval counter 60 as illustrated in FIG. 5. Furthermore, the front wall reflection signal is also applied from the signal conditioning circuit 58 to the delay circuit 66 which provides an output wave form as indicated in FIG. 6 at the portion labelled "simulated inner wall delay". The output of the delay circuit 66 is applied to the inner wall reference pulse circuit 64 which provides an output pulse at the trailing edge of the delay signal, as also illustrated in FIG. 6 of the drawings. The pulse representations on the line entitled "timer/counter" in FIG. 6 illustrate the period between the start of the cunter 60 and the stopping thereof by means of the reference pulse, wherein that stopping signal results in the generation of the marker line illustrated in FIG. 4. Finally, as illustrated in the last wave form shown in FIG. 6 an earlier received stop signals applied to the OR circuit due to reflections from a defect, detected by the oblique transducer, will generate a wave form as illustrated in FIG. 4.

Further details of the background of the invention are described in a Report entitled, *Special Report On Ultrasonic Methods To Detect And Measure Internal Undercut In Pipeline Girth Welds*, PR-140-96, Catalog No. RC8 March, 1980; and *Detection of Internal Undercut In Pipeline Girth Welds*, Catalog No. L51400, November, 1980. Both of such reports are published by the American Gas Association, and both are incorporated herein by reference.

While it is believed that additional embodiments of the invention will become readily apparent to those skilled in the art, it is to be understood that such embodiments are encompassed by the invention, and that the preferred embodiment disclosed herein does not constitute a limitation on the scope of the invention.

I claim:

1. A method for detecting the depth and profile of an internal undercut or toe crack in a pipe-line girth weld, utilizing pulse reflection techniques, comprising the steps of:
    applying ultrasonic pulses of energy to a pipe in said pipe-line, adjacent said weld, at an oblique angle;
    generating a signal simulating received pulses which would be reflected from the inner pipe wall as a result of said obliquely applied pulses of energy;
    detecting all reflected pulses relating to said obliquely applied pulses; and
    providing an indication of the axial position and radial depth within the weld of each reflected pulse which is received prior to the generation of a corresponding simulation pulse, whereby said indication corresponds to profile information related to the position and depth of an internal undercut or crack.

2. A detecting method as set forth in claim 1 further comprising the steps of:
    applying ultrasonic pulses at normal incidence to said pipe, detecting all such normally incident pulses reflected by the outer surface of said pipe, and generating said simulated inner wall signals by applying said reflected normally incident pulses to a delay circuit.

3. A detecting method as set forth in claim 2 wherein said steps of applying oblique and normally incident pulses to said pipe are performed by pulsing respective transducers, and further comprising the step of moving said transducers toward said girth weld, axially of said pipe line, and applying said pulses at different positions along the path of movement of said transducers.

4. A detecting method as set forth in claim 3 wherein said step of providing an indication of each reflected pulse which is received prior to the generation of a corresponding simulation signal is effected by sensing the output of a counter circuit, while applying said simulated and reflected oblique pulses as respective inputs to an OR circuit, applying the output of said OR circuit to a STOP input of said counter, and applying the normally incident reflected pulses to the START input of said counter.

5. A detecting method as set forth in claim 3 further comprising the step of advancing said transducers circumferentially of the girth weld and providing said indications at intervals about said circumference, whereby the circumferential length of each undercut or crack is determined.

6. An apparatus for detecting the depth and profile of an internal undercut or toe crack in a pipe-line girth weld, utilizing pulse reflection techniques, comprising:

means for applying ultrasonic pulses of energy to a pipe in a pipe-line, adjacent said weld, at an oblique angle;

means for generating a signal simulating a received pulse which would be reflected from the inner pipe wall as a result of said obliquely applied pulses of energy;

means for detecting all reflected pulses relating to said obliquely applied pulses; and means for providing an indication of the axial position and radial depth within the weld of each reflected pulse which is received prior to the generation of a corresponding simulation pulse, wherein said indication corresponds to profile information related to the position and depth of an internal undercut or crack.

7. A detecting apparatus as set forth in claim 6, further comprising means for applying ultrasonic pulses at normal incidence to said pipe and for detecting all such normally incident pulses reflected by the outer surface of the pipe, wherein said means for generating said simulated inner wall signals comprises a delay circuit to which said reflected normally incident pulses are applied.

8. A detecting apparatus as set forth in claim 7 wherein said means for applying oblique and normally incident pulses to said pipe comprise respective transducers, and further comprising means for moving said transducers toward said girth weld, axially of said pipe line, and for pulsing said transducers at different positons along the path of movement thereof.

9. A detecting apparatus as set forth in claim 8 wherein said means for providing an indication of each reflected pulse which is received prior to the generation of a corresponding simulation signal comprises: a counter circuit; an OR circuit having its output coupled to a STOP input of said counter circuit, and having respective inputs for receiving said simulated and reflected oblique pulses, wherein a START input of said counter circuit is coupled to receive said normally incident reflected pulses.

10. A detecting apparatus as set forth in claim 8 further comprising means for advancing said transducers circumferentially of the girth weld, wherein said means for providing said indications functions at intervals about said circumference, whereby the circumferential length of each undercut or crack is determined.

* * * * *